(12) United States Patent
Kiyota et al.

(10) Patent No.: US 9,376,657 B2
(45) Date of Patent: Jun. 28, 2016

(54) CULTURE DEVICE

(75) Inventors: Yasujiro Kiyota, Tokyo (JP); Takayuki Uozumi, Machida (JP); Hirofumi Shiono, Fujisawa (JP); Nobuhiko Maiya, Yokohama (JP)

(73) Assignee: NIKON CORPORATION, Tokyo (JP)

(*) Notice: Subject to any disclaimer, the term of this patent is extended or adjusted under 35 U.S.C. 154(b) by 94 days.

(21) Appl. No.: 11/922,486

(22) PCT Filed: Jun. 7, 2006

(86) PCT No.: PCT/JP2006/311424
§ 371 (c)(1),
(2), (4) Date: Dec. 19, 2007

(87) PCT Pub. No.: WO2007/004385
PCT Pub. Date: Jan. 11, 2007

(65) Prior Publication Data
US 2009/0075365 A1    Mar. 19, 2009

(30) Foreign Application Priority Data
Jul. 5, 2005  (JP) .................. 2005-196070

(51) Int. Cl.
*C12M 1/00* (2006.01)
*C12M 3/00* (2006.01)
(52) U.S. Cl.
CPC .............. *C12M 41/14* (2013.01); *C12M 23/48* (2013.01)
(58) Field of Classification Search
CPC .............................. C12M 41/14; C12M 23/48
USPC ........................................... 435/286.2, 303.1
See application file for complete search history.

(56) References Cited

U.S. PATENT DOCUMENTS

| | | | |
|---|---|---|---|
| 4,090,921 A * | 5/1978 | Sawamura et al. | 435/286.2 |
| 4,356,967 A * | 11/1982 | Lunick | 237/14 |
| 5,489,771 A * | 2/1996 | Beach et al. | 250/205 |
| 6,177,271 B1 * | 1/2001 | Butts et al. | 435/303.1 |
| 6,555,365 B2 * | 4/2003 | Barbera-Guillem et al. | 435/303.1 |
| 7,141,413 B2 | 11/2006 | Yamamoto et al. | |
| 7,799,559 B2 | 9/2010 | Hasegawa et al. | |
| 8,110,394 B2 | 2/2012 | Hasegawa et al. | |
| 2004/0101954 A1* | 5/2004 | Graessle et al. | 435/288.7 |

(Continued)

FOREIGN PATENT DOCUMENTS

| | | |
|---|---|---|
| EP | 1 804 107 A1 | 7/2007 |
| JP | A 60-137279 | 7/1985 |

(Continued)

OTHER PUBLICATIONS

Oct. 2, 2012 Office Action issued in Japanese Patent Application No. 2007-523385 (with English Translation).

(Continued)

*Primary Examiner* — Jonathan Hurst
(74) *Attorney, Agent, or Firm* — Oliff PLC

(57) ABSTRACT

A culture device containing a culture vessel for culturing a cell, in which the culture device includes a thermostatic vessel having a stacker containing a plurality of culture vessels for culturing a cell, and an observation portion arranged to be isolated from an atmosphere at inside of the thermostatic vessel and having an object lens, an object lens drive portion, and a camera portion to observe a cell at inside of the culture vessel installed at an observation position at inside of the thermostatic vessel.

12 Claims, 6 Drawing Sheets

(56) References Cited

U.S. PATENT DOCUMENTS

| | | | |
|---|---|---|---|
| 2004/0223213 A1 | 11/2004 | Fukuyama et al. | |
| 2005/0068614 A1* | 3/2005 | Yoneyama et al. | 359/368 |
| 2005/0084420 A1* | 4/2005 | Osawa et al. | 422/99 |
| 2005/0122576 A1* | 6/2005 | Yonetani et al. | 359/370 |

FOREIGN PATENT DOCUMENTS

| | | |
|---|---|---|
| JP | A 11-344676 | 12/1999 |
| JP | A 2004-180675 | 7/2004 |
| JP | A-2005-03720 | 1/2005 |
| JP | A-2005-128443 | 5/2005 |
| JP | A 2005-168341 | 6/2005 |
| JP | A 2005-234306 | 9/2005 |
| JP | A-2005-326495 | 11/2005 |
| JP | A 2006-34256 | 2/2006 |
| WO | WO 2006/033273 A1 | 3/2006 |

OTHER PUBLICATIONS

Oct. 21, 2015 Office Action issued in European Patent Application No. 06757131.5.

* cited by examiner

CULTURE DEVICE

This application is a U.S. National Stage application claiming the benefit of prior filed International Application Number PCT/JP2006/311424, filed Jun. 7, 2006, in which the International Application claims a priority date of Jul. 5, 2005 based on prior filed Japanese Application Number 2005-196070, the entire contents of which are incorporated herein by reference.

TECHNICAL FIELD

The present invention relates to a culture device containing a culture vessel for culturing cells.

BACKGROUND ART

In a background art, there is known a culture device arranged with a stacker including a number of shelves at inside of a thermostatic vessel maintained in a predetermined atmosphere for culturing cells in culture vessels contained in the respective shelves. Further, according to the culture device, an observation portion having a microscope is provided at inside of the thermostatic vessel, and cells in the culture vessels are observed at inside of the thermostatic vessel (refer to For example, Patent Document 1).

Patent Document 1: Japanese Unexamined Patent Application Publication No. 2004-180675

DISCLOSURE

Problems to be Solved

However, when the observation portion is provided at inside of the thermostatic vessel and cells in the culture vessels are going to be observed by the microscope, there poses a problem that a temperature at inside of the thermostatic vessel rises by heat generated from a motor for operating the microscope, illumination means for observation or the like.

The invention has been carried out in order to resolve the problem of the background art and it is an object thereof to provide a culture device capable of reducing a thermal influence of an observation portion on inside of a thermostatic vessel.

Means for Solving the Problems

A culture device according to a first aspect of the invention is characterized in including a thermostatic vessel including a stacker for containing a plurality of culture vessels for culturing a cell and an observation portion arranged to be isolated from an atmosphere at inside of the thermostatic vessel and having an object lens, an object lens drive portion, and a camera portion to observe the cell at inside of the culture vessel installed at an observation position at inside of the thermostatic vessel.

The culture device according to a second aspect of the invention is characterized in that the thermostatic vessel includes at inside a transferring unit provided between the stacker and the observation position for transferring the culture vessel to the observation position, wherein the observation portion observes the cell at inside of the culture vessel transferred to the observation position in the culture device according to the first aspect of the invention.

The culture device according to a third aspect of the invention is characterized in that the thermostatic vessel includes at inside a stage portion for positioning the observation position of the culture vessel transferred by the transferring unit in the culture device according to the first aspect of the invention.

The culture device according to a fourth aspect of the invention is characterized in that the observation portion is provided at a lower portion of the thermostatic vessel, wherein the observation portion includes an illumination device for irradiating illuminating light to an observation sample, and the illumination device is arranged to project inside of the thermostatic vessel in the culture device according to the first aspect of the invention.

The culture device according to a fifth aspect of the invention is characterized in that the illumination device includes a light source, wherein the light source is arranged at a region inside of the observation portion arranged being projected inside of the thermostatic vessel, or inside of the observation portion at a lower portion of the thermostatic vessel in the culture device according to the fourth aspect of the invention.

The culture device according to a sixth aspect of the invention is characterized in that the illumination device is isolated from both of the observation portion provided at the lower portion of the thermostatic vessel and the thermostatic vessel in the culture device according to the fourth aspect of the invention.

The culture device according to a seventh aspect of the invention is characterized in that the light source of the illumination device is provided at outside of the thermostatic vessel and the observation portion in the culture device according to the sixth aspect of the invention.

The culture device according to an eighth aspect of the invention is characterized in that the light source of the illumination device is installed in a plurality of pieces, and one of the plurality of pieces of light sources is installed at a region inside of the observation portion arranged being projected inside of the thermostatic vessel in the culture device according to the fourth aspect of the invention.

The culture device according to a ninth aspect of the invention is characterized in that the thermostatic vessel includes an opening portion to observe an object to be detected by the observation portion, the opening portion being arranged with a transparent member in the culture device according to the first aspect of the invention.

The culture device according to a tenth aspect of the invention is characterized in that the transparent member includes a dew condensation preventing unit for preventing a dew from being condensed to the transparent member in the culture device according to a ninth aspect of the invention.

The culture device according to an eleventh aspect of the invention is characterized in that the observation portion includes a macro observing unit and a micro observing unit in the culture device according to the first aspect of the invention.

The culture device according to a twelfth aspect of the invention is characterized in that the illumination device at inside of the observation portion provided to project to the thermostatic vessel includes an imaging unit for taking an image of a specimen installed at the observation position in the culture device according to the fourth aspect of the invention.

DETAILED DESCRIPTION OF THE EMBODIMENTS

Embodiments of the invention will be explained in details in reference to the drawings as follows.
(First Embodiment)

Figure 1:
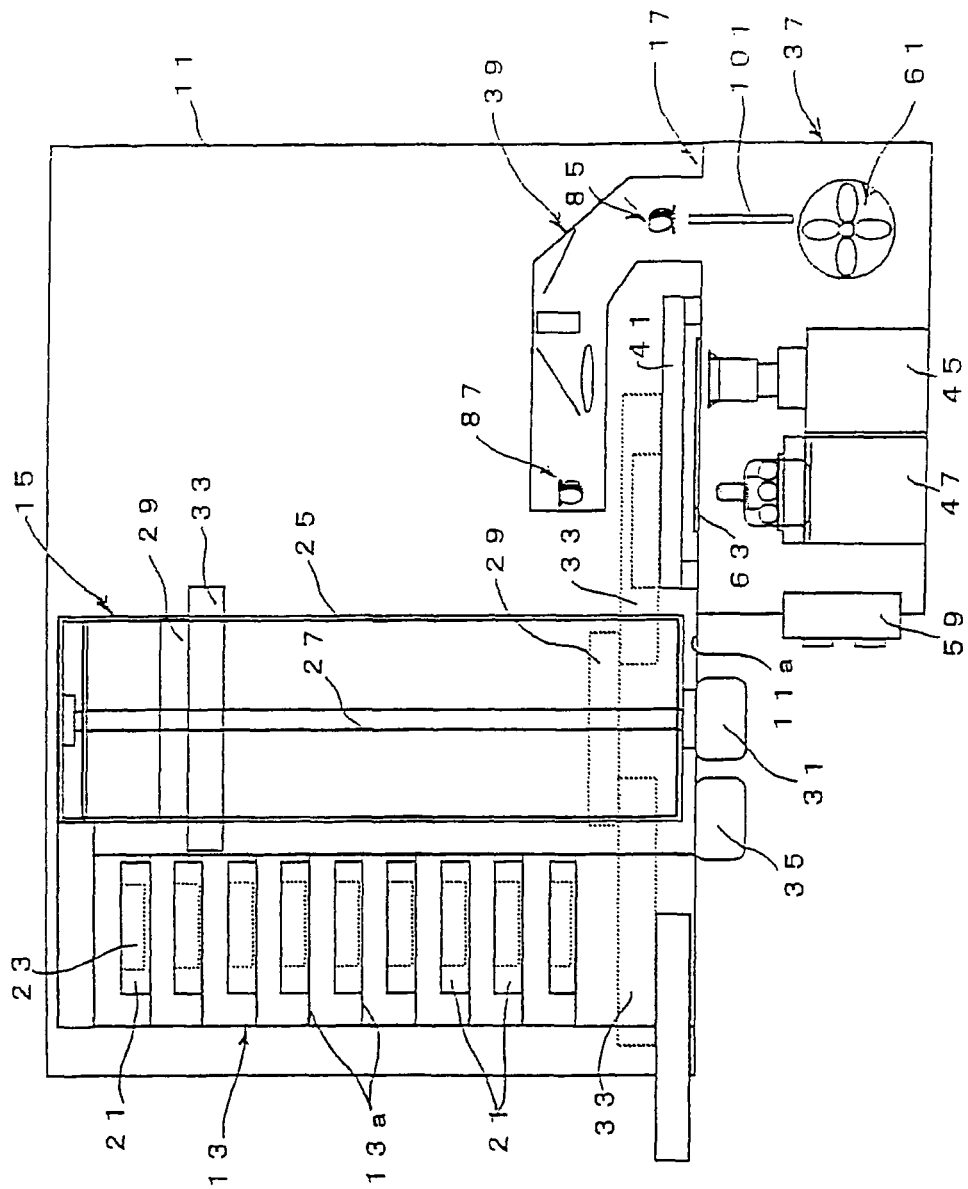
FIG. 1 is an explanatory view showing a first embodiment of a culture device of the invention.

FIG. 1 shows a first embodiment of a culture device of the invention.

The culture device includes a thermostatic vessel 11 maintained in an atmosphere of constant temperature and constant humidity.

Inside of the thermostatic vessel 11 is arranged with a stacker 13 and a transferring device 15. Further, a lower side of the thermostatic vessel 11 is arranged with an observation device 17.

The stacker 13 is partitioned in an up and down direction by a plurality of shelves 13a. An upper face of each shelf 13a is mounted with a holder 21. A culture vessel 23 for culturing cells is held by each holder 21. A vessel of a well plate, a flask, a dish or the like is used for the culture vessel 23.

The transferring device 15 includes a frame 25. A center of the frame 25 is arranged with a screw shaft 27 in an up and down direction. The screw shaft 27 is screwed with a moving member 29 which is made to be movable in the up and down direction when the screw shaft 27 is rotated by a motor 31. A lower side of the moving member 29 is arranged with a transferring arm 33 moved in the up and down direction along with the moving member 29. The transferring arm 33 is made to be movable in a horizontal direction by a drive mechanism (not illustrated) operated by a motor 35. According to the embodiment, the motors 31, 35 are arranged on an outer side of the thermostatic vessel 11 to prevent a temperature at inside of the thermostatic vessel 11 from rising by heat generated by the motors 31, 35.

The observation device 17 includes an observation portion 37, an illumination portion 39 and a stage portion 41. The observation portion 37 is arranged on a lower side of a bottom face 11a of the thermostatic vessel 11. The illumination portion 39 and the stage portion 41 are arranged at inside of the thermostatic vessel 11.

Figure 2:
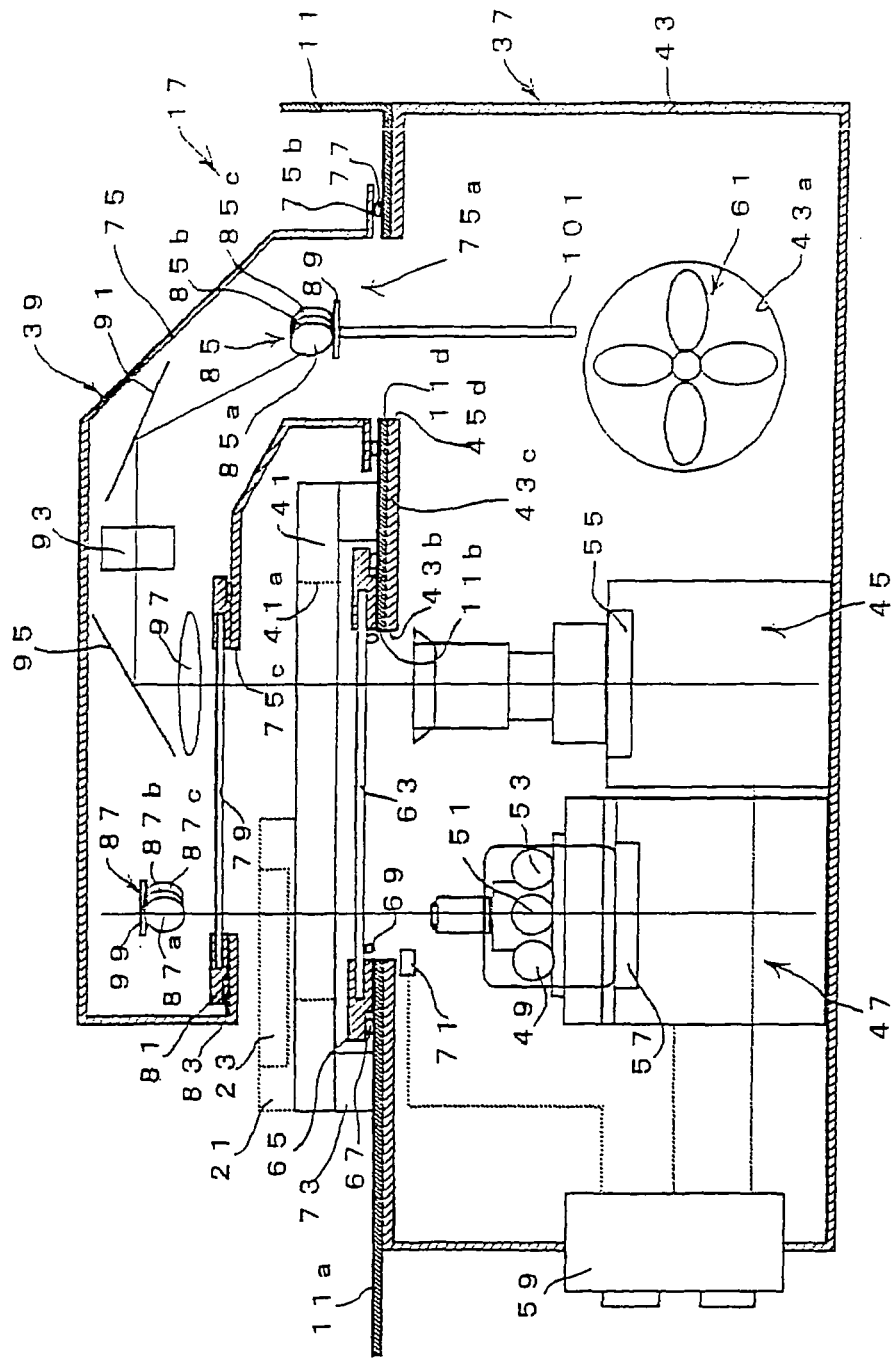
FIG. 2 is an explanatory view showing details of an observation device of FIG. 1.

FIG. 2 shows details of the observation device 17.

The observation portion 37 includes a microscope casing 43. Inside of the microscope casing 43 is arranged with a macro microscope 45 constituting macro observation means and a micro microscope 47 constituting micro observation means. The macro microscope 45 is made to be able to observe, for example, a range of 20 mm square once. Thereby, a distribution of raising cells at inside of the culture vessel 23 can totally be observed. The micro microscope 47 is provided with an observation magnification in correspondence with that of an object lens used in a general microscope. Thereby, cells at inside of the culture vessel 23 can be observed microscopically.

The micro microscope 47 includes a motor 49 for switching the object lens, a motor 51 for focusing, and a motor 53 for driving a middle variable power lens (the middle variable power lens is installed downward from the object lens). The macro microscope 45 and the micro microscope 47 include camera portions 55, 57 having CCD or the like for taking an image to be observed by the microscopes 45, 47.

A side of the microscope casing 43 is arranged with an external interface 59. Drive signals to the motors 49, 51, 53 are outputted byway of the external interface 59. Further, image signals from the camera portions 55, 57 are outputted. A side face of the microscope casing 43 is formed with an opening portion 43a and the opening portion 43a is arranged with an air cooling fan 61. By the air cooling fan 61, air at inside of the microscope casing 43 is exhausted and a temperature at inside of the microscope casing 43 is restrained from rising.

An upper face of the microscope casing 43 is formed with an opening portion 43b at a position upward from the macro microscope 45 and the micro microscope 47. Further, the bottom face 11a of the thermostatic vessel 11 is formed with an opening portion 11b at a position overlapping the opening portion 43b. A transparent member 63 composed of glass, for example, is arranged upward from the opening portion 11b of the thermostatic vessel 11. It is preferable to form a reflection preventing film at the transparent member 63.

The transparent member 63 is supported by a support member 65 in a ring-like shape at an outer periphery thereof. Further, the transparent member 63 is supported by the support member 65 by way of a seal member (not illustrated). A seal member 67 composed of an O ring is arranged between an outer periphery of the support member 65 and the bottom face 11a of the thermostatic vessel 11. Thereby, an atmosphere at inside of the thermostatic vessel 11 and an atmosphere at inside of the microscope casing 43 are isolated.

A lower face of the transparent member 63 is arranged with a heater 69 constituting dew condensation preventing means. Further, a temperature sensor 71 for measuring a temperature at inside of the microscope casing 43 is arranged downward from the heater 69. Further, when the temperature measured by the temperature sensor 71 becomes equal to or lower than, for example, 24° C., electricity is conducted to the heater 69 to prevent condensed dew from adhering to the transparent member 63. That is, inside of the thermostatic vessel 11 is always maintained, for example, at a temperature of about 37° C., and a humidity of about 95%. Therefore, although when the temperature at inside of the microscope casing 43 becomes equal to or lower than, for example, 24° C., condensed dew is adhered to the transparent member 63 and the transparent member 63 is fogged, condensed dew can be prevented from adhering thereto by conducting electricity to the heater 69. Further, electricity may be conducted to the heater 69 only in observing by the macro microscope 45 and the micro microscope 47.

The stage portion 41 is arranged upward from the transparent member 63. The stage portion 41 is made to be movable in the horizontal direction (X direction and Y direction). Further, the culture vessel 23 transferred by the transferring device 15 and held by the holder 21 is positioned. The stage portion 41 is formed with an opening portion 41a for observing cells adhered to a bottom face of the culture vessel 23 from below. Further, the stage portion 41 is supported by the bottom face 11a of the thermostatic vessel 11 by way of a base 73.

The illumination portion 39 is arranged upward from the stage portion 41. The illumination portion 39 includes an illumination casing 75. A lower end of the illumination casing 75 is formed with an opening portion 75a. The opening portion 75a is formed with a flange portion 75b. The flange portion 75b is fixed to the bottom face 11a of the thermostatic vessel 11 by way of a seal member 77 composed of an O ring. Thereby, the atmosphere at inside of the thermostatic vessel 11 and an atmosphere at inside of the illumination casing 75 are isolated. Further, the bottom face 11a of the thermostatic vessel 11 and an upper face 43c of the microscope casing 43 are formed with opening portions 11d, 45d at positions overlapping the opening portion 75a of the illumination casing 75, and inside of the illumination casing 75 is communicated with inside of the microscope casing 43.

An opening portion 75c is formed at a position upward from the stage portion 41 of the illumination casing 75. A transparent member 79 composed of glass is arranged upward from the opening portion 75c. The transparent member 79 is supported by a support member 81 in a ring-like shape at an outer periphery thereof. The transparent member 79 is supported by the support member 81 by way of a seal member (not illustrated). A seal member 83 composed of an O ring is arranged between an outer periphery of the support member 81 and the illumination casing 75. Thereby, the atmosphere at inside of the thermostatic vessel 11 and the atmosphere at inside of the illumination casing 75 are isolated.

Inside of the illumination casing 75 is arranged with a light emitting portion 85 for the macro microscope 45 and a light emitting portion 87 for the micro microscope 47. A board 89 of the light emitting portion 85 for the macro microscope 45 is arranged with LEDs 85a, 85b, 85c of red, blue, green. Light from the light emitting portion 85 is guided to an upper side of the macro microscope 45 by way of a reflecting mirror 91, an electric diaphragm 93, a reflecting mirror 95. Further, cells at inside of the culture vessel 23 are illuminated thereby by way of a lens 97 and the transparent member 79. A board 99 of the light emitting portion 87 for the micro microscope 47 is arranged with LEDs 87a, 87b, 87c of red, blue, green. Cells at inside of the culture vessel 23 are illuminated by light from light emitting portion 87 by way of the transparent member 79. The illumination is carried out by successively making LEDs 85a, 85b, 85c or 87a, 87b, 87c of red, blue, green emit light. Thereby, cells can be observed by a plurality of wavelengths of light and cells having different light absorption bands can firmly be observed.

One end of a heat pipe 101 is arranged at a vicinity of the board 89 of the light emitting portion 85 for the macro microscope 45 and other end thereof is extended to a vicinity of the cooling fan 61. By the heat pipe 101, heat generated at the light emitting portion 85 is guided to the cooling fan 61 and transferred out from inside of the microscope casing 43. Further, it is preferable to provide a heat pipe also at a vicinity of the light emitting portion 87 for the micro microscope 47 to guide heat generated at the light emitting portion 87 to the cooling fan 61.

According to the above-described culture device, by the transferring arm 33 of the transferring device 15, the holder 21 holding the culture vessel 23 is transferred to the stage portion 41. Further, first, the culture vessel 23 held by the holder 21 is made to be disposed upward from the macro microscope 45 by moving the stage portion 41 and observation by the macro microscope 45 is carried out by irradiating light from the light emitting portion 85 to the culture vessel 23. Next, the culture vessel 23 held by the holder 21 is made to be disposed upward from the micro microscope 47 by moving the stage portion 41, and observation by the micro microscope 47 is carried out by irradiating light from the light emitting portion 87 to the culture vessel 23.

According to the above-described culture device, the observation portion 37 is arranged on the lower side of the bottom face 11a of the thermostatic vessel 11 to be isolated from the atmosphere at inside of the thermostatic vessel 11, and therefore, a thermal influence of the observation portion 37 to inside of the thermostatic vessel 11 can be reduced.

Further, the transferring device 15 for transferring the holder 21 holding the culture vessel 23 to the stage portion 41 is arranged at inside of the thermostatic vessel 11 and in a side direction relative to a position of installing a sample of the stage portion 41, and therefore, the culture vessel 23 is moved to the stage portion 41 in the horizontal direction, and therefore, the culture vessel 23 which needs to be observed can easily be transferred to the stage portion 41.

Further, since the stage portion 41 movable in the horizontal direction is provided, the culture vessel 23 can firmly be disposed at a position upward from the macro microscope 45 or micro microscope 47.

Further, according to the above-described culture device, the heater 69 is provided downward from the transparent member 63, and therefore, dew can firmly be prevented from being condensed to the transparent member 63.

Further, the observation portion 37 is arranged with the macro microscope 45 and the micro microscope 47, and therefore, a distribution of raising cells as well as details of cells at inside of the culture vessel 23 can firmly be observed.

Further, the illumination portion 39 is arranged to be isolated from the atmosphere at inside of the thermostatic vessel 11, and the illumination portion 39 is communicated with inside of the observation portion 37 by the opening portion 75a, and therefore, a thermal influence of the illumination portion 39 effected to inside of the thermostatic vessel 11 can be reduced.

Further, there can be constituted a system including a main body of a personal computer (PC) and connecting operating means, a monitor or the like from outside thereto at inside of the microscope casing 43. In this case, the microscope casing 43 becomes a control box. Further, when an apparatus including a thermostatic vessel and a microscope casing is connected to a personal computer by LAN or the like and an operation instruction from the personal computer, a state data from the apparatus or the like is made to be able to be exchanged, the apparatus can remotely be operated.

(Second Embodiment)

Figure 3:
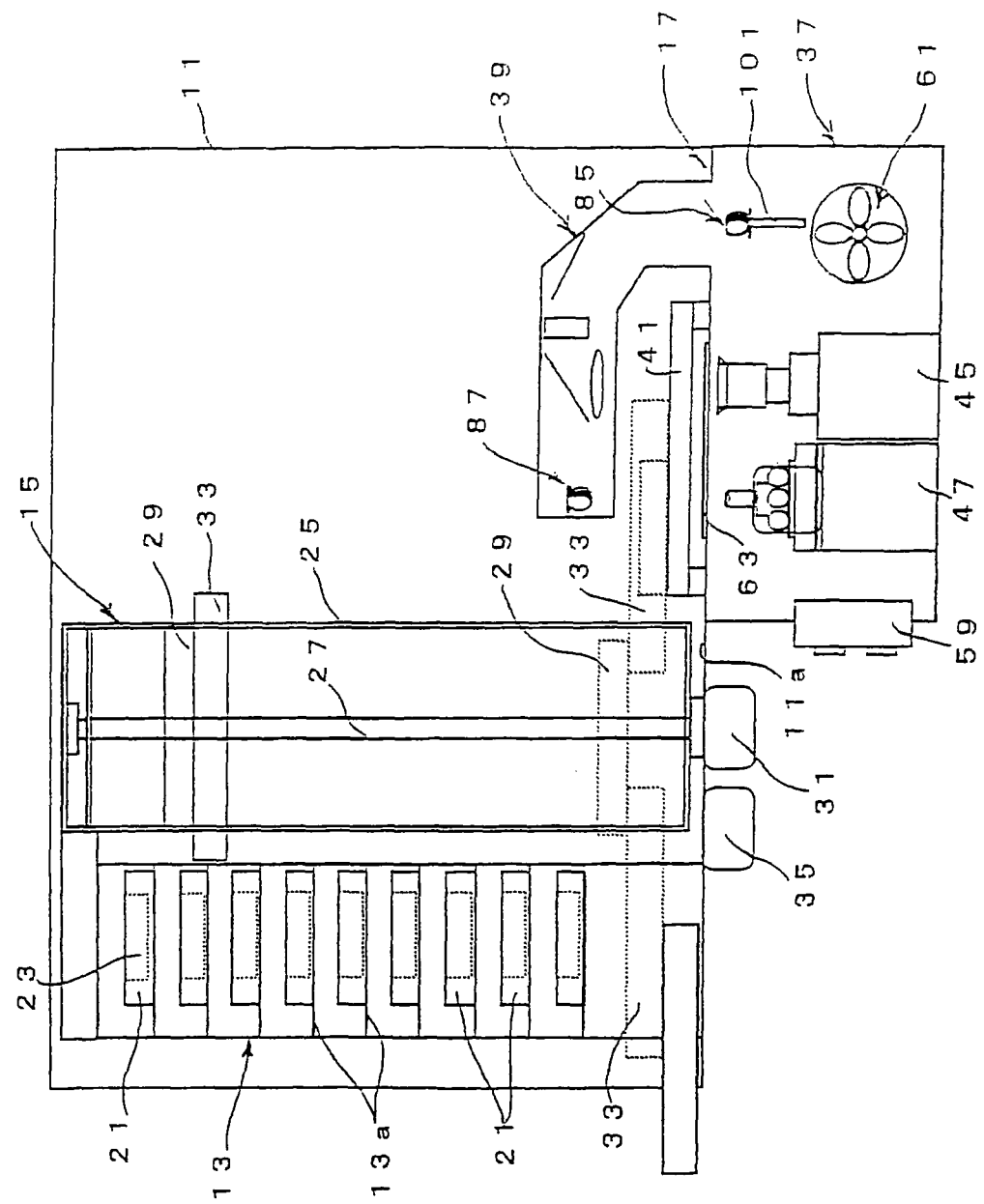
FIG. 3 is an explanatory view showing a second embodiment of a culture device of the invention.

FIG. 3 shows a second embodiment of a culture device of the invention.

Further, in the embodiment, members the same as those of the first embodiment are attached with the same notations and a detailed explanation thereof will be omitted.

According to the embodiment, the light emitting portion 85 constituting a light source for the macro microscope 45 is arranged at inside of the observation portion 37 downward from the thermostatic vessel 11. Further specifically, the light emitting portion 85 is arranged at an upper vicinity of the air cooling fan 61.

That is, in consideration of an influence of heat effected to the atmosphere at inside of the thermostatic vessel 11, it is preferable to install the light emitting portion 85 at inside of the observation portion 37, further, the influence of the heat effected to the atmosphere at inside of the thermostatic vessel 11 can be alleviated by using LED as the light emitting portion 85.

(Third Embodiment)

Figure 4:
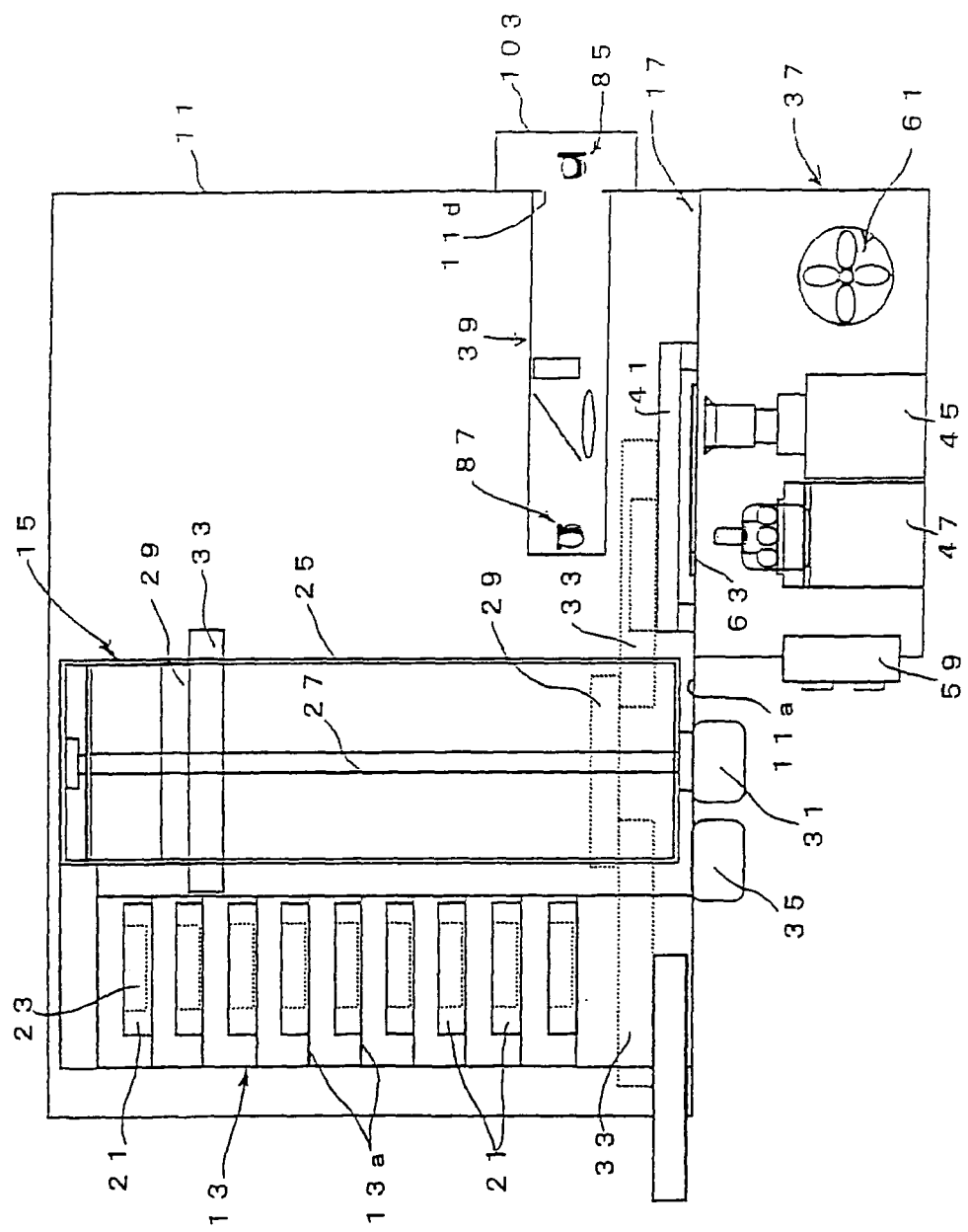
FIG. 4 is an explanatory view showing a third embodiment of a culture device of the invention.

FIG. 4 shows a third embodiment of a culture device of the invention.

Further, in the embodiment, members the same as those of the first embodiment are attached with the same notations and a detailed explanation thereof will be omitted.

According to the embodiment, the light emitting portion 85 constituting the light source for the macro microscope 45 is contained at inside of a cabinet 103 arranged at outside of a side face of the thermostatic vessel 11. The cabinet 103 is not connected to the observation portion 37 but is connected to the illumination portion 39 by way of an opening portion 11d provided at the side face of the thermostatic vessel 11. Supply of power to the illumination portion 39 is carried out from a power supply portion (not illustrated) provided at outside of the observation portion 37 and the thermostatic vessel 11.

According to the embodiment, the influence of the heat generated at the illumination portion 39 effected to both of the observation portion 37 and the thermostatic vessel 11 can further be reduced.

(Fourth Embodiment)

Figure 5:
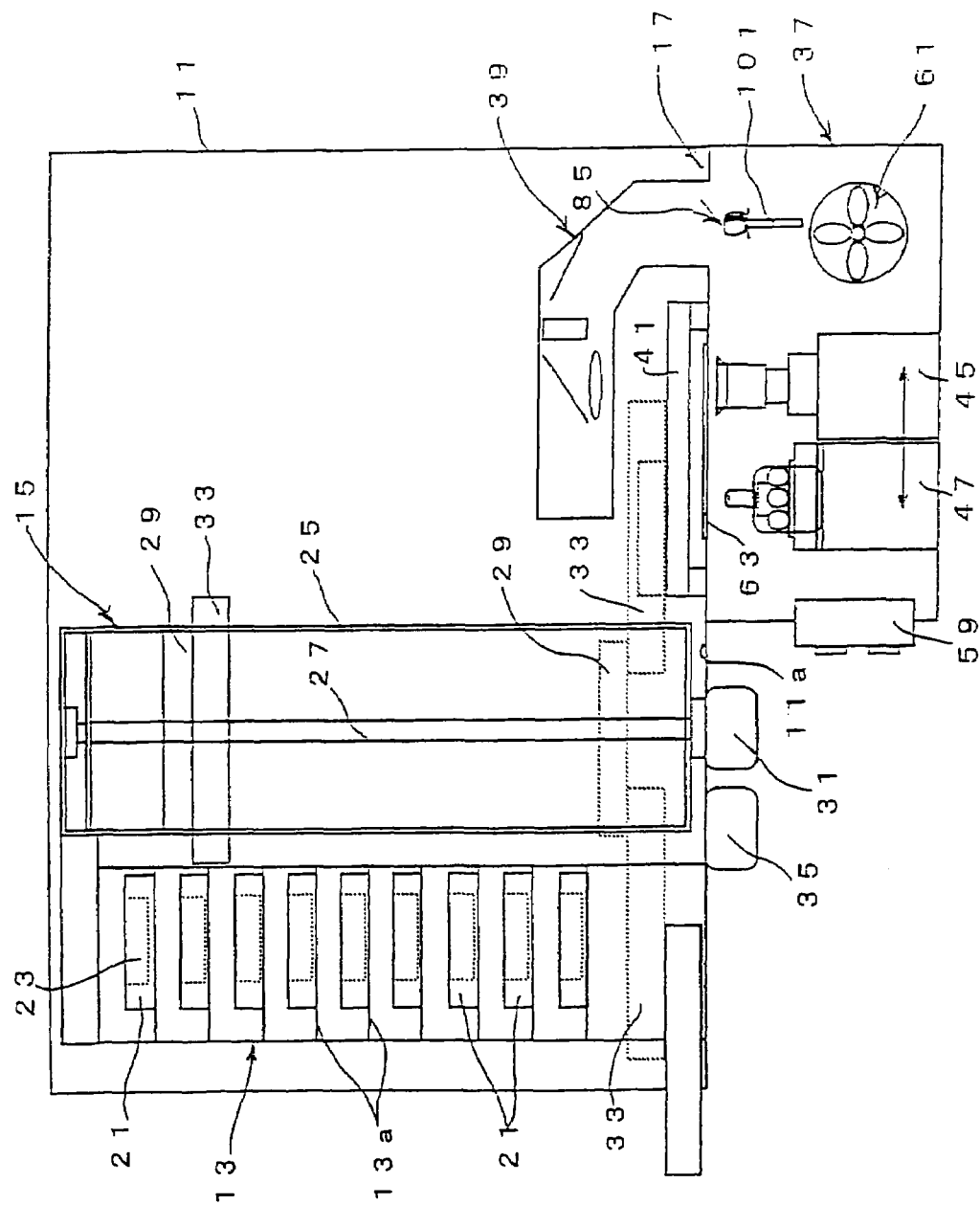
FIG. 5 is an explanatory view showing a fourth embodiment of a culture device of the invention.

FIG. 5 shows a fourth embodiment of a culture device of the invention.

Further, in the embodiment, members the same as those of the first embodiment are attached with the same notations and a detailed explanation thereof will be omitted.

According to the embodiment, similar to the second embodiment, the light emitting portion 85 constituting the light source for the macro microscope 45 is arranged at inside of the observation portion 37 downward from the thermostatic vessel 11. Further, the light emitting portion 87 arranged at inside of the illumination portion 39 in the first embodiment is omitted and the light source of the illuminating portion 39 is constituted only by the light emitting portion 85. Further, the macro microscope 45 and the micro microscope 47 are switched to an observation position by sliding sides of the microscopes 45, 47 by moving means, not illustrated.

According to the embodiment, the light emitting portion 87 is omitted, and therefore, an amount of heat generated at the illumination portion 39 can be reduced.

(Fifth Embodiment)

Figure 6:
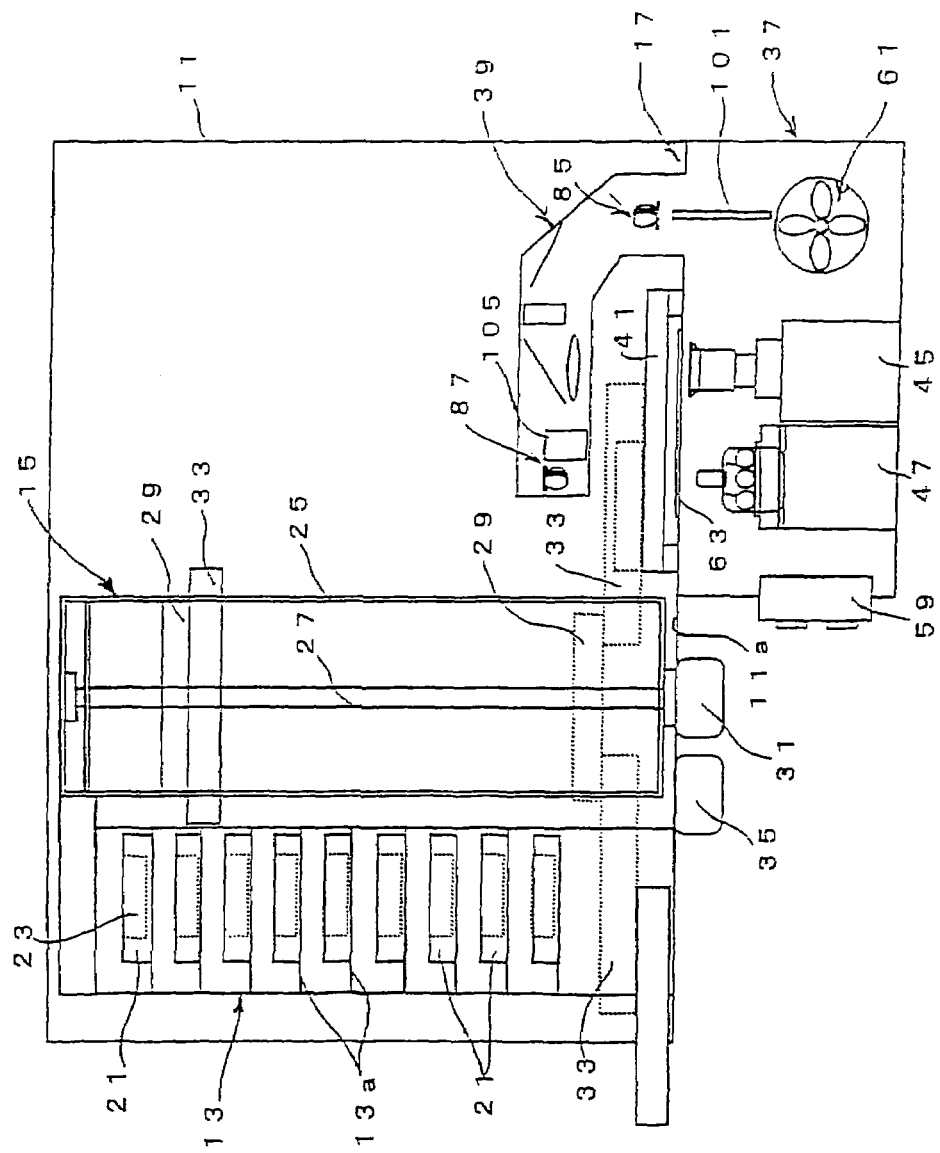
FIG. 6 is an explanatory view showing a fifth embodiment of a culture device of the invention.

FIG. 6 shows a fifth embodiment of a culture device of the invention.

Further, in the embodiment, members the same as those of the first embodiment are attached with the same notations and a detailed explanation thereof will be omitted.

According to the embodiment, inside of the illumination portion 39 provided to project to inside of the thermostatic vessel 11 is arranged with an imaging device 105 for taking an image of a sample to be observed disposed at an observation position to be opposed to the stage portion 41.

According to the embodiment, by taking a macro image of the sample to be observed mounted onto the stage portion 41 by the imaging device 105, the macro image of the sample to be observed mounted at the observation position of the stage portion 41 can be provided. Further, a state of a total of the sample to be observed which cannot be provided by the microscopes 45, 47 can be provided prior to observation by the microscopes 45, 47 and effective information can be provided in the observation by the microscopes 45, 47.

(Supplementary Items of Embodiments)

Although an explanation has been given of the invention by the above-described embodiments as described above, the technical range of the invention is not limited to the above-described embodiments but, for example, the following modes will do.

(1) Although an explanation has been given of an example of providing the observation portion 37 on the lower side of the bottom face 11a of the thermostatic vessel 11, for example, the observation portion 37 may be provided on an outer side of an upper face, a side face or the like of the thermostatic vessel 11 by constituting a condition of being remote from the thermostatic vessel 11. However, in this case, it is indispensable to provide a relay optical system to the respective microscopes.

(2) Although in the above-described embodiments, an explanation has been given of an example of irradiating light from the upper side of the culture vessel 23, for example, light may be irradiated from a lower side of the culture vessel 23.

(3) Although in the above-described embodiments, an explanation has been given of an example of preventing dew from being condensed to the transparent member 63 by the heater 69, for example, a dew condensation preventing film may be coated to the transparent member 63, or both thereof may be used.

(4) Although in the above-described embodiments, an explanation has been given by taking an example of using glass for the transparent member 63, for example, a plastic may be used.

(5) Although in the above-described embodiments, an explanation has been given of an example of using LEDs 85a, 85b, 85c, 87a, 87b, 87c for the light emitting portions 85, 87, for example, a light source normally used in a microscope, or an optical fiber or the like may be used.

The many features and advantages of the embodiments are apparent from the detailed specification and, thus, it is intended by the appended claims to cover all such features and advantages of the embodiments that fall within the true spirit and scope thereof. Further, since numerous modifications and changes will readily occur to those skilled in the art, it is not desired to limit the inventive embodiments to exact construction and operation illustrated and described, and accordingly all suitable modifications and equivalents may be resorted to, falling within the scope thereof.

The invention claimed is:

1. A culture device comprising:
   a thermostatic vessel including a stage portion positioning an observation position of a sample;
   an illumination device including an illumination casing that is isolated from an atmosphere inside of the thermostatic vessel and projected inside of the thermostatic vessel;
   a microscope casing that is arranged on a lower side of a bottom face of the thermostatic vessel such that a temperature inside the microscope casing is isolated from an atmosphere inside the thermostatic vessel; and
   an object lens arranged inside the microscope casing,
   wherein the illumination casing includes at inside a first imaging device taking a macro image of the sample on the stage portion;
   the microscope casing includes at inside a microscope for micro observing and a second imaging device taking an image to be observed by the microscope for micro observing;
   the microscope for micro observing includes a first motor for switching the object lens; and
   the microscope casing further includes at inside a middle variable power lens and a second motor for driving the middle variable power lens.

2. The culture device according to claim 1, wherein the first motor drives the object lens within the microscope casing.

3. The culture device according to claim 1, further comprising a stacker containing a plurality of culture vessels for culturing a cell within the thermostatic vessel.

4. The culture device according to claim 1, further comprising
   a heater and a temperature sensor arranged inside the microscope casing, wherein the temperature sensor measures the temperature inside the microscope casing, and the heater is controlled based on the temperature measured by the temperature sensor.

5. The culture device according to claim 1, further comprising an observation portion that is arranged on the lower side of the bottom face of the thermostatic vessel, the observation portion including a light source, the second imaging device, the middle variable power lens, and the second motor for driving the middle variable power lens.

6. The culture device according to claim 5, wherein the light source is a plurality of LEDs having different emission wavelengths.

7. The culture device according to claim 1, wherein a light from a light source is guided to a predetermined position in the illumination casing, the predetermined position being located opposite side of the object lens with respect to the stage portion in a vertical direction.

8. The culture device according to claim 1, wherein the illumination casing is disposed over the microscope casing.

9. The culture device according to claim 1, wherein there is a space between a projected portion of the illumination casing and an upper portion of the microscope casing so that the stage portion of thermostatic vessel is disposed in the space.

10. The culture device according to claim 1, wherein the thermostatic vessel includes a stacker holding a culture vessel for culturing a cell for observing.

11. The culture device according to claim 10, wherein:
the thermostatic vessel further includes a transferring device transferring the culture vessel inside of the stacker to the stage portion; and
a third motor for driving the transferring device is arranged on an outer side of the thermostatic vessel and the microscope casing.

12. The culture device according to claim 10, wherein the object lens arranged inside the microscope casing includes the first motor for switching the object lens.

* * * * *